(12) United States Patent
Ohno et al.

(10) Patent No.: US 11,760,382 B2
(45) Date of Patent: Sep. 19, 2023

(54) INFORMATION PROCESSING DEVICE, INFORMATION PROCESSING METHOD, AND SYSTEM

(71) Applicant: TOYOTA JIDOSHA KABUSHIKI KAISHA, Toyota (JP)

(72) Inventors: Mitsuyoshi Ohno, Miyoshi (JP); Daiki Kubo, Toyota (JP); Yosuke Nozaki, Toyota (JP); Tsukasa Nakanishi, Nagoya (JP); Hironori Aoyama, Toyota (JP); Seiji Yogo, Nagoya (JP); Tae Sugimura, Miyoshi (JP); Yasuhiro Kobatake, Nagoya (JP); Shinya Kijima, Nagoya (JP); Osamu Fukawatase, Miyoshi (JP); Koji Yasui, Toyota (JP); Toshiyuki Kobayashi, Miyoshi (JP); Hitomi Nakatani, Toyota (JP); Toshinari Ogawa, Nagoya (JP); Kohta Tarao, Nagoya (JP); Kuniaki Jinnai, Nagoya (JP); Sayaka Ninoyu, Toyota (JP); Takeshi Yamada, Anjo (JP); Nobuki Hayashi, Nisshin (JP); Masahiro Nagano, Toyota (JP); Ryo Sato, Nisshin (JP); Akihiro Ito, Tokyo (JP)

(73) Assignee: TOYOTA JIDOSHA KABUSHIKI KAISHA, Toyota (JP)

(*) Notice: Subject to any disclaimer, the term of this patent is extended or adjusted under 35 U.S.C. 154(b) by 366 days.

(21) Appl. No.: 17/162,862

(22) Filed: Jan. 29, 2021

(65) Prior Publication Data
US 2021/0261163 A1    Aug. 26, 2021

(30) Foreign Application Priority Data

Feb. 20, 2020   (JP) .................. 2020-027092

(51) Int. Cl.
| | |
|---|---|
| *B60R 15/04* | (2006.01) |
| *G01N 33/00* | (2006.01) |
| *B60W 60/00* | (2020.01) |

(52) U.S. Cl.
CPC ......... *B60W 60/0025* (2020.02); *B60R 15/04* (2013.01); *B60W 2300/00* (2013.01);
(Continued)

(58) Field of Classification Search
CPC .. E03D 5/00; E03D 7/00; B60R 15/04; B63B 29/14
See application file for complete search history.

(56) References Cited

U.S. PATENT DOCUMENTS

| | | | |
|---|---|---|---|
| 10,932,630 B1* | 3/2021 | Luu | ............................ E03D 7/00 |
| 2012/0221192 A1* | 8/2012 | Seibt | .................. G01N 21/6456 |
| | | | 296/24.3 |

(Continued)

FOREIGN PATENT DOCUMENTS

| | | |
|---|---|---|
| CN | 102733466 A | 10/2012 |
| JP | 07-227368 A | 8/1995 |

*Primary Examiner* — Peter D Nolan
*Assistant Examiner* — Anwar Mohamed
(74) *Attorney, Agent, or Firm* — Sughrue Mion, PLLC

(57) ABSTRACT

An information processing device for managing a vehicle including a toilet unit, a tank unit connected to the toilet unit for storing waste that flows from the toilet unit, and a traveling unit capable of moving the toilet unit and the tank unit. The information processing device performs control for disconnecting the traveling unit from the toilet unit and the tank unit when installing a toilet. The information processing device includes a control unit configured to acquire a storage amount of waste in the tank unit and to generate commands to the traveling unit to cause the traveling unit to replace the tank unit when the storage amount of waste becomes equal to or larger than a predetermined amount.

18 Claims, 9 Drawing Sheets

(52) U.S. Cl.
CPC ..... *B60W 2420/42* (2013.01); *B60W 2420/52* (2013.01); *B60W 2510/30* (2013.01); *G01N 33/0062* (2013.01)

(56) References Cited

U.S. PATENT DOCUMENTS

| | | | |
|---|---|---|---|
| 2019/0056751 A1 | 2/2019 | Ferguson et al. | |
| 2019/0343358 A1* | 11/2019 | Davis | G05D 1/0088 |
| 2021/0059489 A1* | 3/2021 | Luu | E03D 7/00 |
| 2021/0261163 A1* | 8/2021 | Ohno | B60W 60/0025 |
| 2022/0369872 A1* | 11/2022 | Prescott | A47K 11/026 |
| 2023/0045671 A1* | 2/2023 | van Zuijlen | E03D 13/00 |
| 2023/0064596 A1* | 3/2023 | Niemela | A47K 11/02 |

* cited by examiner

| TOILET UNIT ID | LOCATION |
|---|---|
| A01 | L11 |
| A02 | L12 |
| A03 | L13 |
| A04 | L14 |
| ... | ... |

| TANK UNIT ID | LOCATION |
|---|---|
| B01 | L11 |
| B02 | L12 |
| B03 | L13 |
| B04 | L14 |
| ... | ... |

FIG. 8
| TRAVELING UNIT ID | LOCATION | MOVING ROUTE | TOILET UNIT ID | TANK UNIT ID |
|---|---|---|---|---|
| C01 | L31 | D01 | E01 | F01 |
| C02 | L32 | D02 | E02 | F02 |
| C03 | L33 | D03 |  | F03 |
| C04 | L34 | D04 |  |  |
| ... | ... | ... | ... | ... |
FIG. 9
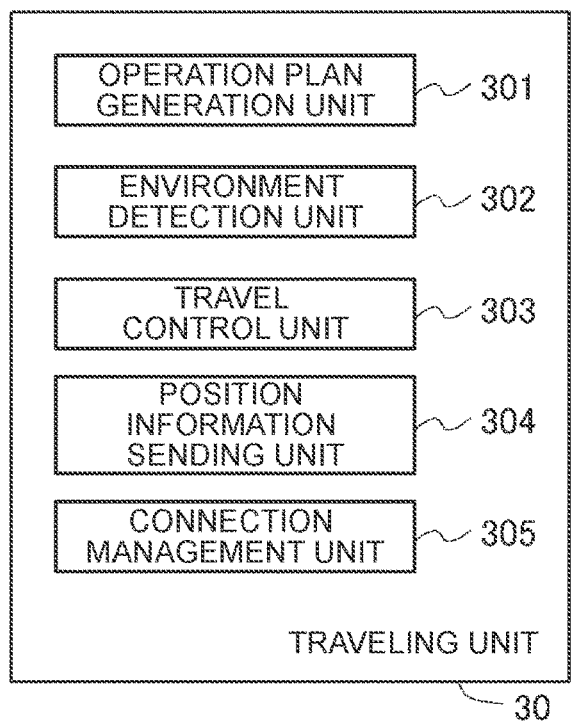
FIG. 10
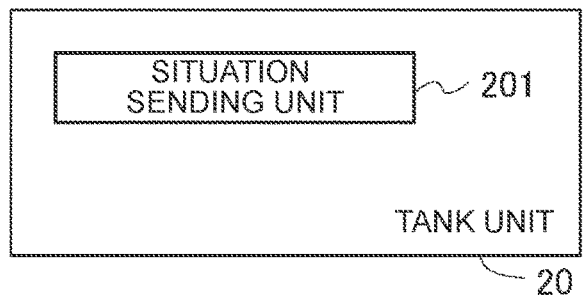

INFORMATION PROCESSING DEVICE, INFORMATION PROCESSING METHOD, AND SYSTEM

INCORPORATION BY REFERENCE

The disclosure of Japanese Patent Application No. 2020-027092 filed on Feb. 20, 2020 including the specification, drawings and abstract is incorporated herein by reference in its entirety.

BACKGROUND

1. Technical Field

The present disclosure relates to an information processing device, an information processing method, and a system.

2. Description of Related Art

A technique for a temporary toilet is known (for example, see Japanese Unexamined Patent Application Publication No. 7-227368 (JP 7-227368 A)).

SUMMARY

The present disclosure provides a technique for improving the operation of a temporary toilet.

A first aspect of the present disclosure relates to an information processing device for managing a vehicle including a toilet unit, a tank unit connected to the toilet unit for storing waste that flows from the toilet unit, and a traveling unit capable of moving the toilet unit and the tank unit. The information processing device is a device for performing control for disconnecting the traveling unit from the toilet unit and the tank unit when installing a toilet. The information processing device includes a control unit configured to acquire a storage amount of waste in the tank unit and to generate commands to the traveling unit to cause the traveling unit to replace the tank unit when the storage amount of waste becomes equal to or larger than a predetermined amount.

A second aspect of the present disclosure relates to an information processing method for managing a vehicle including a toilet unit, a tank unit connected to the toilet unit for storing waste that flows from the toilet unit, and a traveling unit capable of moving the toilet unit and the tank unit. The information processing method is a method for performing control for disconnecting the traveling unit from the toilet unit and the tank unit when installing a toilet. The information processing method is performed by a computer and includes acquiring a storage amount of waste in the tank unit and generating commands to the traveling unit to cause the traveling unit to replace the tank unit when the storage amount of waste becomes equal to or larger than a predetermined amount.

A third aspect of the present disclosure relates to a system including a vehicle and a server. The vehicle includes a toilet unit, a tank unit connected to the toilet unit for storing waste that flows from the toilet unit, and a traveling unit capable of moving the toilet unit and the tank unit. The server includes a control unit configured to perform control for disconnecting the traveling unit from the toilet unit and the tank unit when installing a toilet. The control unit is configured to acquire a storage amount of waste in the tank unit and to generate commands to the traveling unit to cause the traveling unit to replace the tank unit when the storage amount of waste becomes equal to or larger than a predetermined amount.

Another aspect of the present disclosure relates to a program that causes a computer to perform the information processing method described above or relates to a storage medium that stores therein the program permanently.

According to the present disclosure, the operation of a temporary toilet is improved.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein:

FIG. 8 is a diagram showing an example of the table configuration of traveling unit information;

FIG. 9 is a diagram showing an example of the functional configuration of the traveling unit;

FIG. 10 is a diagram showing an example of the functional configuration of the tank unit;

DETAILED DESCRIPTION OF EMBODIMENTS

A traveling unit travels autonomously according to commands generated by a control unit of an information processing device that is one aspect of the present disclosure. The traveling unit can carry a toilet unit and a tank unit together, or can carry a tank unit only. The traveling unit, which travels according to the commands, can carry the toilet unit and the tank unit to the installation place of the toilet. In addition, the traveling unit, which travels according to the commands, can carry the tank unit to the installation place of the toilet.

The control unit acquires the storage amount of waste of the tank unit and, when the storage amount of waste becomes equal to or larger than a predetermined amount, generates commands to the traveling unit to cause the traveling unit to replace the tank unit. The predetermined amount mentioned here is, for example, the storage amount of waste that is a threshold at which the tank unit is to be replaced. The traveling unit performs operation to replace the tank unit according to the commands generated by the control unit, making it possible to prevent the amount of waste stored in the tank from becoming too large. In addition, after one toilet is installed, the traveling unit can carry another toilet or can carry a tank unit to be used for replacement. This means that more toilets can be operated by a smaller number of traveling units.

Embodiments of the present disclosure will be described below with reference to the drawings. Noe that the configuration of the embodiments given below is an example and the present disclosure is not limited to the configuration of the embodiments. In addition, the embodiments described below can be combined as much as possible.

First Embodiment

Figure 1:
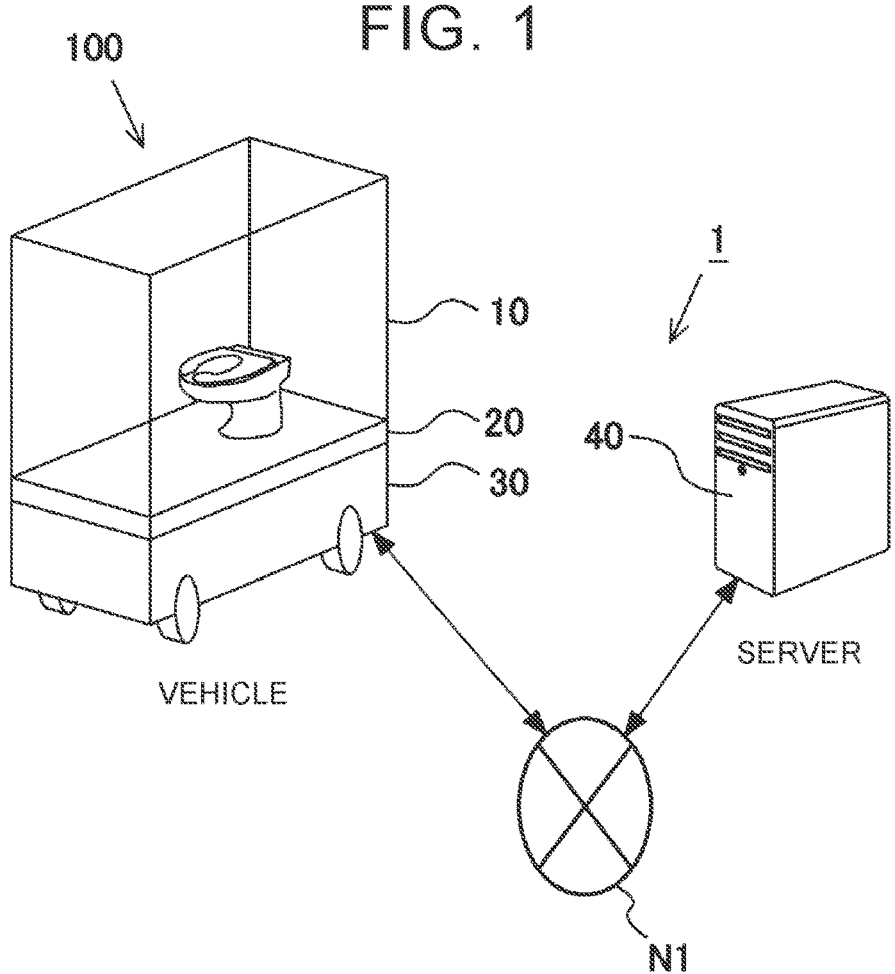
FIG. 1 is a diagram showing the schematic configuration of an autonomous driving system according to an embodiment.

FIG. 1 is a diagram showing the schematic configuration of an autonomous driving system 1 according to an embodiment. The autonomous driving system 1 includes, for example, a vehicle 100 and a server 40. The vehicle 100 includes a toilet unit 10, a tank unit 20, and a traveling unit 30. The toilet unit 10 and the tank unit 20 can be connected and disconnected. The tank unit 20 and the traveling unit 30 can be connected and disconnected. Furthermore, the toilet unit 10 can be connected to, and disconnected from, a different tank unit 20, the tank unit 20 can be connected to, and disconnected from, a different toilet unit 10 and a different traveling unit 30, and the traveling unit 30 can be connected to, or disconnected from, a different tank unit 20. Although one unit is shown for each of the toilet unit 10, tank unit 20, and traveling unit 30 in the example in FIG. 1, two or more units may be included for each of them. The traveling unit 30 can travel autonomously according to operation commands generated by the server 40. The toilet unit 10, tank unit 20, and traveling unit 30, though arranged vertically in FIG. 1, may be arranged in the front-rear direction or in the left-right direction of the traveling direction of the vehicle 100.

The toilet unit 10 in FIG. 1 is a unit used by a user as a toilet and is equipped, for example, with a toilet seat. The toilet unit 10 can be accessed by users who use the toilet. The tank unit 20 is a unit for storing waste flowing from the toilet unit 10. The traveling unit 30 can carry the toilet unit 10 and the tank unit 20 together or can carry the tank unit 20 only.

Figure 2:
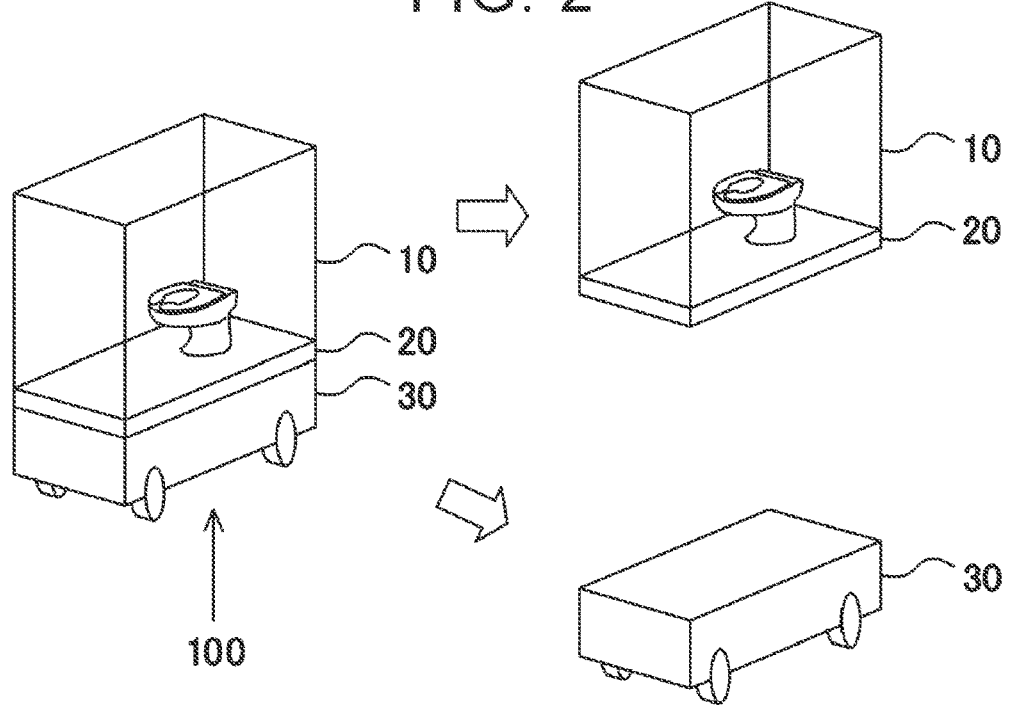
FIG. 2 is a diagram showing how the members of a vehicle are disconnected when a toilet is installed.

When a temporary-toilet installation request is received, the traveling unit 30 installs the toilet unit 10 and the tank unit 20 at a user-desired place according to the command received from the server 40. FIG. 2 is a diagram showing how the members of the vehicle 100 are disconnected when a toilet is installed. When the vehicle 100 arrives at the installation place of the toilet, the vehicle 100 is divided into two parts, a part composed of the toilet unit 10 and the tank unit 20 and a part composed of the traveling unit 30, as indicated by the white arrows. Then, the toilet unit 10 and the tank unit 20 are left there and function as a temporary toilet. On the other hand, the traveling unit 30 can leave the place for carrying another toilet unit 10 and another tank unit 20.

Figure 3:
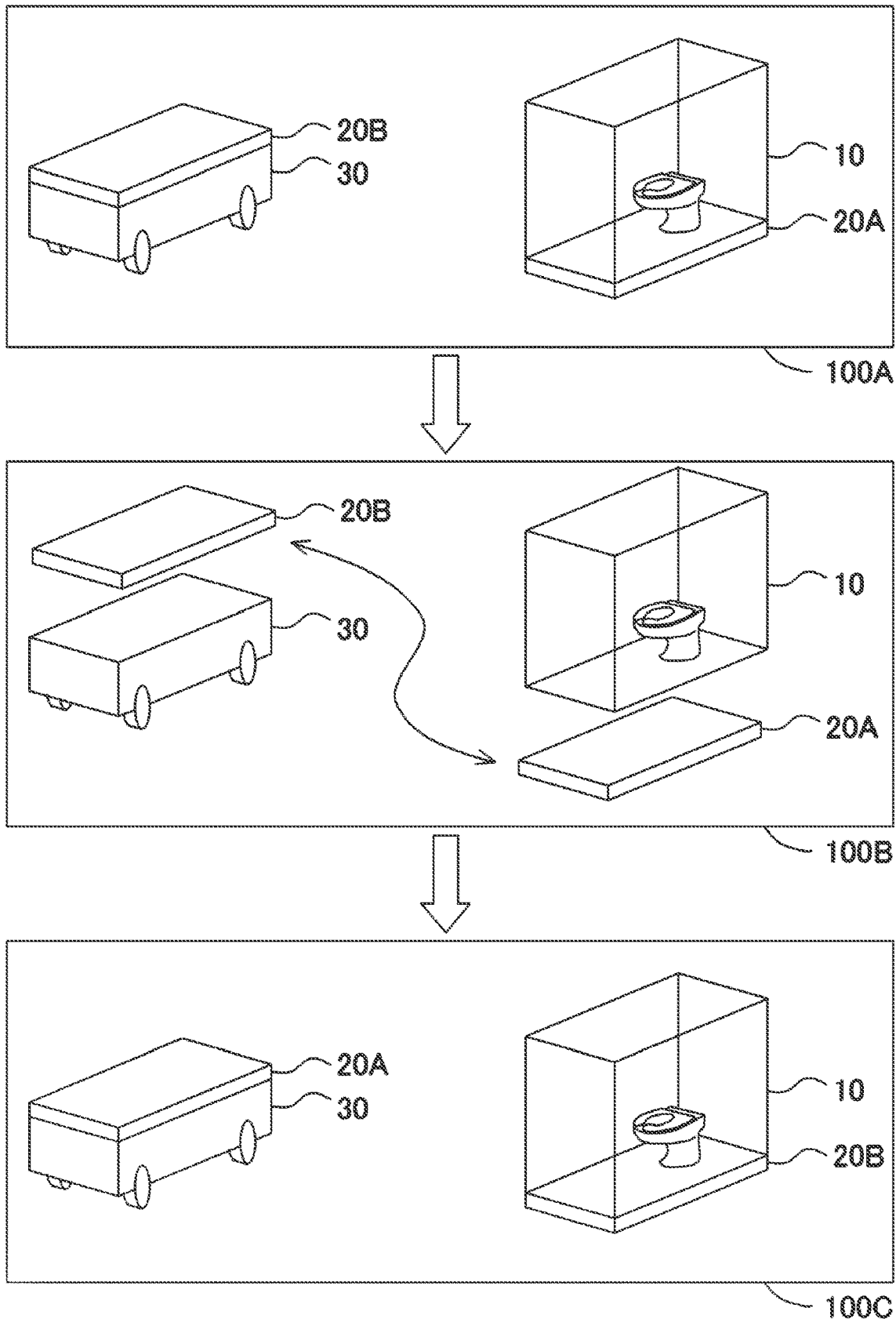
FIG. 3 is a diagram showing how a traveling unit replaces a tank unit.

In addition, the traveling unit 30 can replace the tank unit 20. FIG. 3 is a diagram showing how the traveling unit 30 replaces the tank unit 20. A reference numeral 20A indicates a tank unit with a storage amount of waste equal to or larger than a predetermined amount (hereinafter referred to as a tank unit to be replaced), and a reference numeral 20B indicates an empty tank unit. When there is no need to distinguish between the tank unit to be replaced 20A and the empty tank unit 20B, they are simply referred to as the tank unit 20. In 100A in FIG. 3, the traveling unit 30 to which the empty tank unit 20B is connected is traveling autonomously to the place where there are the toilet unit 10 and the tank unit to be replaced 20A. In 100B in FIG. 3, the empty tank unit 20B is disconnected from the traveling unit 30, the tank unit to be replaced 20A is disconnected from the toilet unit 10, and the tank unit to be replaced 20A is replaced with the empty the tank 20B. In 100C in FIG. 3, the tank unit to be replaced 20A and the traveling unit 30 are connected, and the traveling unit 30 carries the tank unit to be replaced 20A, for example, to a waste treatment plant. On the other hand, the toilet unit 10 and the empty tank unit 20B are connected to function as a temporary toilet at that place.

The tank unit 20, the traveling unit 30, and the server 40 are connected to each other by a network N1. As the network N1, a WAN (Wide Area Network), which is a world-wide public communication network such as the Internet, or another communication network may be used. The network N1 may include a telephone communication network such as a mobile phone network and a wireless communication network such as WiFi.

Hardware Configuration

Figure 4:
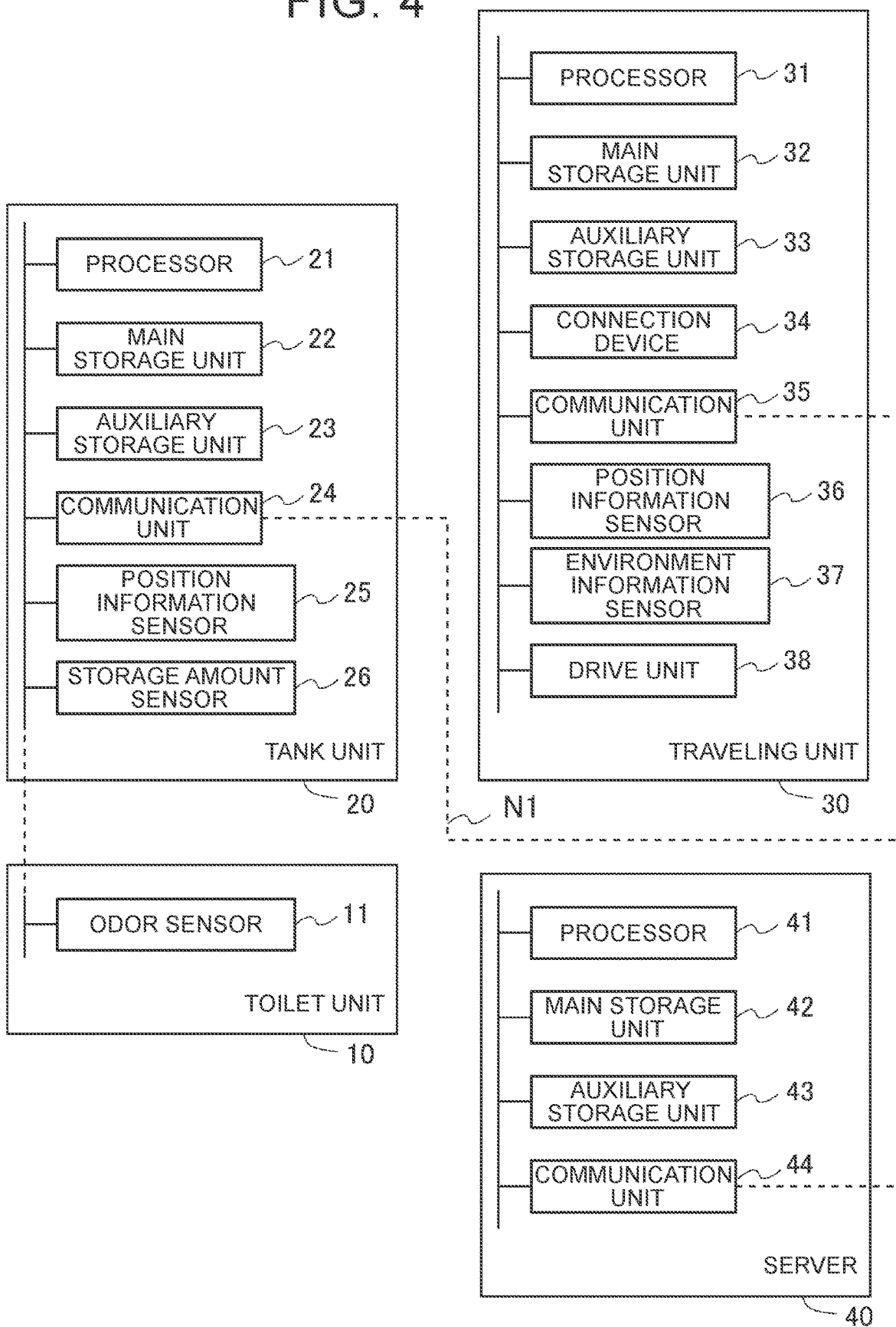
FIG. 4 is a block diagram schematically showing an example of the configuration of each of a toilet unit, a tank unit, a traveling unit, and a server that configure an autonomous driving system according to the embodiment.

The hardware configuration of the toilet unit 10, tank unit 20, traveling unit 30, and server 40 will be described with reference to FIG. 4. FIG. 4 is a block diagram schematically showing an example of the configuration of the toilet unit 10, tank unit 20, traveling unit 30, and server 40 that configure the autonomous driving system 1 according to this embodiment.

The server 40 has a general computer configuration. The server 40 includes a processor 41, a main storage unit 42, an auxiliary storage unit 43, and a communication unit 44. These units are connected to each other by a bus. The server 40 is an example of an "information processing device".

The processor 41 is a central processing unit (CPU), a digital signal processor (DSP), or the like. The processor 41 controls the server 40 for performing various information processing operations. The processor 41 is an example of a "control unit". The main storage unit 42 is a random access memory (RAM), a read only memory (ROM), or the like. The auxiliary storage unit 43 is an erasable programmable ROM (EPROM), a hard disk drive (HDD), a removable medium, or the like. The auxiliary storage unit 43 stores the operating system (OS), various programs, various tables, and so on. The processor 41 loads programs from the auxiliary storage unit 43 into the work area of the main storage unit 42 for execution and, through this program execution, controls the components. Controlling the components in this way allows the server 40 to implement the functions that satisfy the predetermined purpose. The main storage unit 42 and the auxiliary storage unit 43 are computer-readable recording media. The server 40 may be a single computer or a plurality of computers that work together. The information stored in the auxiliary storage unit 43 may also be stored in the main storage unit 42. Conversely, the information stored in the main storage unit 42 may be stored in the auxiliary storage unit 43.

The communication unit 44 is a unit for communicating with the tank unit 20 and the traveling unit 30 via the network N1. The communication unit 44 is, for example, a local area network (LAN) interface board or a wireless communication circuit for wireless communication. The LAN interface board or the wireless communication circuit is connected to the network N1.

A series of processing performed by the server 40 can be performed by hardware or software. The hardware configuration of the server 40 is not limited to that shown in FIG. 4. In addition, a part or all of the components of the server 40 may be installed in the tank unit 20 or in the traveling unit 30.

Next, the traveling unit 30 will be described. The traveling unit 30 includes a processor 31, a main storage unit 32, an auxiliary storage unit 33, a connection device 34, a communication unit 35, a position information sensor 36, an environment information sensor 37, and a drive unit 38. These units are connected to each other by a bus. The processor 31, main storage unit 32, auxiliary storage unit 33, and communication unit 35 are similar to the processor 41, main storage unit 42, auxiliary storage unit 43, and communication unit 44 of the server 40 and, therefore, the description thereof is omitted.

The connection device 34 is a device that performs the connection and disconnection of the toilet unit 10, tank unit 20, and traveling unit 30 based on control commands generated by the processor 31. For example, the connection device 34 has an electromagnet, a slope, a rail, or a crane for connecting the tank unit 20 to the traveling unit 30. The connection device 34 can also disconnect the tank unit 20 connected to the toilet unit 10 and, then, connect another tank unit 20 to the toilet unit 10. For example, the connection device 34 has an actuator that operates when the tank unit 20 is connected to, or disconnected from, the traveling unit 30. Note that the method for connecting between the toilet unit 10 and the tank unit 20 and for connecting between the tank unit 20 and the traveling unit 30 is not limited to a particular method but any method may be used.

The communication unit 35 is a communication unit for connecting the traveling unit 30 to the network N1. The communication unit 35 is a circuit for communicating with another unit (for example, the server 40 or the tank unit 20, etc.) via the network N1, using a mobile communication service (for example, a telephone communication network conforming to the standard such as the 5th generation (5G) standard, 4th generation (4G) standard, 3rd generation (3G) standard, or Long Term Evolution (LTE) standard) or using a wireless communication such as Wi-Fi (registered trademark) or Bluetooth (registered trademark).

The position information sensor 36 acquires the position information (for example, latitude and longitude) on the traveling unit 30 at a predetermined cycle. The position information sensor 36 is, for example, a Global Positioning System (GPS) receiver, a wireless communication unit, or the like. The information acquired by the position information sensor 36 is recorded, for example, in the auxiliary storage unit 33, and is sent to the server 40.

The environment information sensor 37 is a unit for sensing the state of the traveling unit 30 or for sensing the surroundings of the traveling unit 30. Sensors for sensing the state of the traveling unit 30 include an acceleration sensor, a speed sensor, and an azimuth sensor. Sensors for sensing the surroundings of the traveling unit 30 include a stereo camera, a laser scanner, a LIDAR, a radar, or the like.

The drive unit 38 causes the traveling unit 30 to travel based on control commands generated by the processor 31. The drive unit 38 is configured to include, for example, a motor and an inverter for driving the wheels of the traveling unit 30, a brake mechanism, a steering mechanism, and so on. The traveling unit 30 travels autonomously when the motor, the brake mechanism, or any other mechanism is driven by control commands.

Next, the tank unit 20 will be described. The tank unit 20 includes a processor 21, a main storage unit 22, an auxiliary storage unit 23, a communication unit 24, a position information sensor 25, and a storage amount sensor 26. These units are connected to each other by a bus. In addition, the tank unit 20 has a tank capable of storing waste. The processor 21, main storage unit 22, auxiliary storage unit 23, communication unit 24, and position information sensor 25 of the tank unit 20 are similar to the processor 31, the main storage unit 32, and the auxiliary storage unit 33, communication unit 35, and the position information sensor 36 of the traveling unit 30 and, therefore, the description thereof is omitted.

The storage amount sensor 26 is a sensor that detects the storage amount of waste stored in the tank unit 20. The storage amount sensor 26 may be a sensor that detects the weight of waste, a sensor that detects the water level, or a sensor that detects the number of times waste has flowed from the toilet unit 10.

Next, the toilet unit 10 will be described. The toilet unit 10 has an odor sensor 11 that detects an odor in the toilet unit 10. When the toilet unit 10 is connected to the tank unit 20, the interface of the toilet unit 10 and the interface of the tank unit 20 are connected. When these interfaces are connected, the detection value of the odor sensor 11 is passed to the tank unit 20. The odor sensor 11 is not an essential component.

Functional Configuration: Server

Figures 5, 6, 7:
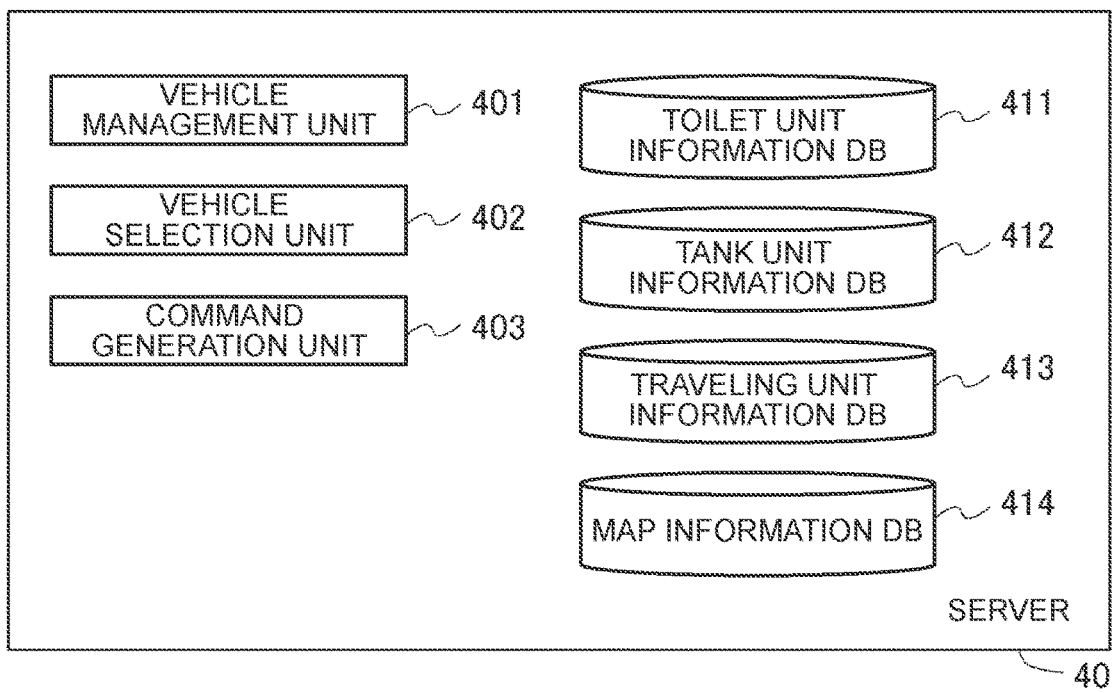
FIG. 5 is a diagram showing an example of the functional configuration of the server.
FIG. 6 is a diagram showing an example of the table configuration of toilet unit information.
FIG. 7 is a diagram showing an example of the table configuration of tank unit information.

FIG. 5 is a diagram showing an example of the functional configuration of the server 40. The server 40 includes the following functional components: a vehicle management unit 401, a vehicle selection unit 402, a command generation unit 403, a toilet unit information DB 411, a tank unit information DB 412, a traveling unit information DB 413, and a map information DB 414. The vehicle management unit 401, vehicle selection unit 402, and command generation unit 403 are functional components provided, for example, when the processor 41 of the server 40 executes various programs stored in the auxiliary storage unit 43.

The toilet unit information DB 411, tank unit information DB 412, traveling unit information DB 413, and map information DB 414 are, for example, relational databases. These relational databases are built by managing the data, stored in the auxiliary storage unit 43, by the programs of the database management system (DBMS) that are executed by the processor 41. Note that any of the functional components of the server 40 or a part of the processing thereof may be performed by another computer connected to the network N1.

The vehicle management unit 401 manages various type of information on the toilet unit 10, the tank unit 20, and the traveling unit 30. For example, the vehicle management unit 401 manages the locations of the toilet unit 10, the tank unit 20, and the traveling unit 30. The location is represented, for example, by latitude and longitude. For example, the vehicle management unit 401 acquires and manages the position information sent from the tank unit 20 at a predetermined cycle, or the position information sent from the tank unit 20 in response to a request from the server 40. In addition, the vehicle management unit 401 acquires and manages the position information sent from the traveling unit 30 at a predetermined cycle, or the position information sent from the traveling unit 30 in response to a request from the server 40.

When the toilet unit 10 is in the state connected to the tank unit 20, the position information on the connected toilet unit 10 is considered to be the same as the position information on the tank unit 20. Similarly, when the tank unit 20 is in the state connected to the traveling unit 30, the position information on the connected the tank unit 20 may be considered to be the same as the position information on the traveling unit 30. When the toilet unit 10 and the tank unit 20 are in the state disconnected from the traveling unit 30, the position information on the toilet unit 10 and the tank unit 20 may be considered to be the same as the position information on the traveling unit 30 at the time when the toilet unit 10 and the tank unit 20 were disconnected from the traveling unit 30. Note that considering the position information on the toilet unit 10, tank unit 20, and traveling unit 30 as described above may eliminate the need for the position information sensor 25 of the tank unit 20. The vehicle management unit 401 stores the position information on the toilet unit 10 in the toilet unit information DB 411 in association with the toilet unit ID. The toilet unit ID is an identifier unique to the toilet unit 10. The vehicle management unit 401 stores the position information on the tank unit 20 in the tank unit information DB 412 in association with the tank unit ID. The tank unit ID is an identifier unique to the tank unit 20. The vehicle management unit 401 stores the position information on the traveling unit 30 in the traveling unit information DB 413, which will be described later, in association with the traveling unit ID. The traveling unit ID is an identifier unique to the traveling unit 30.

When a usage request is received from a user terminal, the vehicle selection unit 402 selects the toilet unit 10, the tank unit 20, and the traveling unit 30. A usage request is the information sent from a user to request the installation of a temporary toilet. The usage request includes, for example, the information on the place where the temporary toilet is to be installed and the information on the requesting user. The requesting method is not limited to a particular method but any requesting method may be used. The vehicle selection unit 402 accesses the toilet unit information DB 411, tank unit information DB 412, traveling unit information DB 413, and map information DB 414 to select the toilet unit 10, tank unit 20 and the traveling unit 30 that are available for use.

For example, to install the toilet unit 10 and the tank unit 20 at the installation place of the temporary toilet, the vehicle selection unit 402 selects a combination of the toilet unit 10, tank unit 20, and traveling unit 30 all of which are within a predetermined moving distance of the traveling unit 30. When there is a plurality of such combinations, the vehicle selection unit 402 selects a combination that minimizes the cost, a combination that minimizes the moving distance of the traveling unit 30, or a combination that minimizes the time required to install the temporary toilet. After selecting the toilet unit 10, tank unit 20, and traveling unit 30, the vehicle selection unit 402 updates the traveling unit information DB 413 that will be described later.

For example, when selecting the toilet unit 10 and tank unit 20, the vehicle selection unit 402 may select the toilet unit 10 and the tank unit 20 existing in the area within a first predetermined distance from the installation place of the temporary toilet. The first predetermined distance is a distance within which the toilet unit 10 and the tank unit 20 can move. The first predetermined distance is determined, for example, according to the cost or according to the time required to install the temporary toilet. When there is a plurality of selectable toilet units 10 and tank units 20, the vehicle selection unit 402 may select the toilet unit 10 and the tank unit 20 that have the shortest moving distance to the installation place of the temporary toilet or may randomly select the toilet unit 10 and the tank unit 20. The vehicle selection unit 402 may also select the toilet unit 10 and the tank unit 20 that minimize the cost.

Similarly, when selecting the traveling unit 30, the vehicle selection unit 402 may select the traveling unit 30 existing in the area within a second predetermined distance from the locations of the toilet unit 10 and the tank unit 20. The second predetermined distance is a distance within which the traveling unit 30 can move. The second predetermined distance is determined according to the cost or according to the time required to install the temporary toilet. When there is a plurality of selectable traveling units 30, the vehicle selection unit 402 may select the traveling unit 30 that has the shortest moving distance from the location of the traveling unit 30 to the locations of the toilet unit 10 and the tank unit 20 or may randomly select the traveling unit 30. The vehicle selection unit 402 may also select the traveling unit 30 that minimizes the cost.

In addition, when the tank unit 20 of the temporary toilet needs to be replaced, the vehicle selection unit 402 selects the empty tank unit 20B and the traveling unit 30. Whether the tank unit 20 needs to be replaced is determined based on the detection value of the storage amount sensor 26 sent from the tank unit 20. For example, when the detection value of the storage amount sensor 26 is equal to or larger than a predetermined amount, the vehicle selection unit 402 determines that the tank unit 20 needs to be replaced and selects the empty tank unit 20B and the traveling unit 30.

Also in this case, to replace the tank unit 20, the vehicle selection unit 402 selects a combination of the tank unit 20 and the traveling unit 30 both of which are within a predetermined moving distance of the traveling unit 30. When there is a plurality of such combinations, the vehicle selection unit 402 selects a combination that minimizes the cost, a combination that minimizes the moving distance of the traveling unit 30, or a combination that minimizes the time required to replace the tank unit 20. After selecting the tank unit 20 and the traveling unit 30, the vehicle selection unit 402 updates the traveling unit information DB 413 that will be described later.

Instead of the selection method described above, the vehicle selection unit 402 may select the empty tank unit 20B existing in the area within the first predetermined distance from the installation place of the temporary toilet. Furthermore, the vehicle selection unit 402 may select the traveling unit 30 existing in the area within the second predetermined distance from the location of the empty tank unit 20B.

When the traveling unit 30 carries the toilet unit 10 and the tank unit 20 to the installation place of a temporary toilet, the command generation unit 403 generates the operation commands that cause the traveling unit 30, for example, to start at the starting location (base) and, via the location of the toilet unit 10, the location the tank unit 20, and the installation place of the toilet, to return to the starting location (base). On the other hand, when the tank unit 20 is replaced, the command generation unit 403 generate the operation commands that cause the traveling unit 30, for example, to start at the starting location (base) and, via the location of the empty tank unit 20B and the location of the tank unit to be replaced 20A, to return to the starting location (base).

The command generation unit 403 according to this embodiment generates a moving route based on the map information stored in the map information DB 414 that will be described later. The generated moving route is a route generated according to a predetermined rule that is intended to minimize the moving distance of the traveling unit 30 or to minimize the moving time of the traveling unit 30. The command generation unit 403 sends the operation commands, which include the moving route, to the traveling unit 30. In addition, the command generation unit 403 stores the generated moving route in the traveling unit information DB 413 that will be described later.

The toilet unit information DB 411 is formed by storing the information on the toilet unit 10 (hereinafter also referred to as "toilet unit information") in the auxiliary storage unit 43. The configuration of the toilet unit information stored in the toilet unit information DB 411 will be described below with reference to FIG. 6. FIG. 6 is a diagram showing an example of the table configuration of the toilet unit information. The toilet unit information table has the toilet unit ID field and the location field. The toilet unit ID field contains the identification information identifying the toilet unit 10. The location field contains the information on the location of the toilet unit 10. When the toilet unit 10 is disconnected from the traveling unit 30, the location of the toilet unit 10 may remain unchanged until the next time the toilet unit 10 is connected to the traveling unit 30.

The tank unit information DB 412 is formed by storing the information on the tank unit 20 (hereinafter also referred to as "tank unit information") in the auxiliary storage unit 43. The configuration of the tank unit information stored in the tank unit information DB 412 will be described below with reference to FIG. 7. FIG. 7 is a diagram showing an example of the table configuration of the tank unit information. The tank unit information table has the tank unit ID field and the location field. The tank unit ID field contains the identification information identifying the tank unit 20. The location field contains the information on the location of the tank unit 20. When the tank unit 20 is disconnected from the traveling unit 30, the location of the tank unit 20 may remain unchanged until the next time the tank unit 20 is connected to the traveling unit 30.

The traveling unit information DB 413 is formed by storing the information on the traveling unit 30 (hereinafter also referred to as "traveling unit information") in the auxiliary storage unit 43. The configuration of the traveling unit information stored in the traveling unit information DB 413 will be described below with reference to FIG. 8. FIG. 8 is a diagram showing an example of the table configuration of the traveling unit information. The traveling unit information table has the traveling unit ID field, location field, moving route field, toilet unit ID field, and tank unit ID field. The traveling unit ID field contains the identification information identifying the traveling unit 30. The location field contains the information on the location of the traveling unit 30. The moving route field contains the information on the moving route of the traveling unit 30. The moving route is generated by the command generation unit 403. The toilet unit ID field contains the toilet unit ID of the toilet unit 10 being carried by the traveling unit 30 or the toilet unit ID of the toilet unit 10 to be carried by the traveling unit 30. When the traveling unit 30 is not scheduled to carry the toilet unit 10, the toilet unit ID field is left blank. The tank unit ID field contains the tank unit ID of the tank unit 20 being carried by the traveling unit 30 or the tank unit ID of the tank unit 20 to be carried by the traveling unit 30. When the traveling unit 30 is not scheduled to carry the tank unit 20, the tank unit ID field is left blank. When the vehicle selection unit 402 combines the toilet unit 10 or the tank unit 20 with the traveling unit 30, the vehicle selection unit 402 updates the toilet unit ID field or the tank unit ID field that is a field of the traveling unit information DB 413 and that corresponds to the traveling unit 30.

The map information DB 414 stores the map information including the map data and the point of interest (POI) information represented by characters and photographs showing the characteristics of each point on the map data. The map information DB 414 may be provided from another system, for example, from Geographic Information System (GIS) connected to the network N1.

Functional Configuration: Traveling Unit

FIG. 9 is a diagram showing an example of the functional configuration of the traveling unit 30. The traveling unit 30 includes the following functional components: an operation plan generation unit 301, an environment detection unit 302, a travel control unit 303, a position information sending unit 304, and a connection management unit 305. The operation plan generation unit 301, environment detection unit 302, travel control unit 303, position information send unit 304, and connection management unit 305 are functional components provided, for example, when the processor 31 of the traveling unit 30 executes various programs stored in the auxiliary storage unit 33.

The operation plan generation unit 301 acquires operation commands from the server 40 and generates its own operation plan. The operation commands include the information on the moving route of the traveling unit 30. The operation plan generation unit 301 calculates the route of the traveling unit 30 based on the operation commands received from the server 40, and generates an operation plan for moving on the calculated route.

The environment detection unit 302 detects the environment around the traveling unit 30, which is necessary for autonomous traveling, based on the data acquired by the environment information sensor 37. The objects detected by the environment detection unit 302 include, but are not limited to, the number of lanes and their positions, the number other moving objects around the traveling unit 30 and their positions, the number of obstacles around the traveling unit 30 (for example, pedestrians, bicycles, structures, and buildings) and their positions, the structure of roads, and road signs. The environment detection unit 302 may detect any object as long as it is necessary for autonomous traveling. For example, when the environment information sensor 37 is a stereo camera, the image data captured by the stereo camera is image-processed for detecting the objects around the traveling unit 30. The data on the surrounding environment of the traveling unit 30, detected by the environment detection unit 302 (hereinafter, environmental data), is sent to the travel control unit 303 that will be described later.

The travel control unit 303 generates control commands for controlling the autonomous traveling of the traveling unit 30, based on the operation plan generated by the operation plan generation unit 301, the environmental data generated by the environment detection unit 302, and the position information on the traveling unit 30 acquired by the position information sensor 36. For example, the travel control unit 303 generates control commands that cause the traveling unit 30 in such a way that the traveling unit 30 will travel along the predetermined route and in a predetermined safety area around the traveling unit 30 where obstacles do not enter. The generated control commands are sent to the drive unit 38. A known method may be used as a method for generating control commands for autonomously moving the traveling unit 30.

The position information sending unit 304 sends the position information, acquired from the position information sensor 36, to the server 40 via the communication unit 35. The position information sending unit 304 may send the position information any time. For example, the position information sending unit 304 may send the position information regularly, at the same time another piece of information is sent to the server 40, or in response to a request from the server 40. The position information sending unit 304 sends the position information to the server 40 together with the traveling unit ID.

The connection management unit 305 generates commands regarding connection and disconnection between the toilet unit 10, the tank unit 20, and the traveling unit 30. These commands include the following commands: a command that causes the connection device 34 to perform an operation to connect the toilet unit 10 and the tank unit 20 to the traveling unit 30, a command that causes the connection device 34 to perform an operation to connect the tank unit 20 to the traveling unit 30, a command that causes the connection device 34 to perform an operation to disconnect the toilet unit 10 and the tank unit 20 from the traveling unit 30, and a command that causes the connection device 34 to perform an operation to disconnect the tank unit 20 from the traveling unit 30. The commands may also include a command that causes the connection device 34 to perform an operation to replace the tank unit 20.

Functional Configuration: Tank Unit

FIG. 10 is a diagram showing an example of the functional configuration of the tank unit 20. The tank unit 20 includes a situation sending unit 201 as the functional component. The situation sending unit 201 is a functional component provided, for example, when the processor 21 of the tank unit 20 executes various programs stored in the auxiliary storage unit 23.

The situation sending unit 201 sends the position information, acquired from the position information sensor 25, to the server 40 via the communication unit 24. The situation sending unit 201 may send the position information any time. For example, the situation sending unit 201 may send the position information regularly, at the same time another piece of information is sent to the server 40, or in response to a request from the server 40. The situation sending unit 201 sends the position information to the server 40 together with the tank unit ID. Note that, when the tank unit 20 is in the state connected to the traveling unit 30, the position information on the connected the tank unit 20 may be considered to be the same as the position information on the traveling unit 30 as described above. In this case, by using the position information on the traveling unit 30 as the position information on the tank unit 20, the sending of the position information from the tank unit 20 may be omitted.

The situation sending unit 201 also sends the detection value of the storage amount sensor 26 and the detection value of the odor sensor 11 to the server 40 via the communication unit 24. The situation sending unit 201 may send the detection values of these sensors any time. For example, the situation sending unit 201 may send the detection values regularly, at the same time another piece of information is sent to the server 40, or in response to a request from the server 40. The situation sending unit 201 sends the detection values of the sensors to the server 40 together with the tank ID.

Processing Flow when Installing Temporary Toilet: Server

Figure 11:
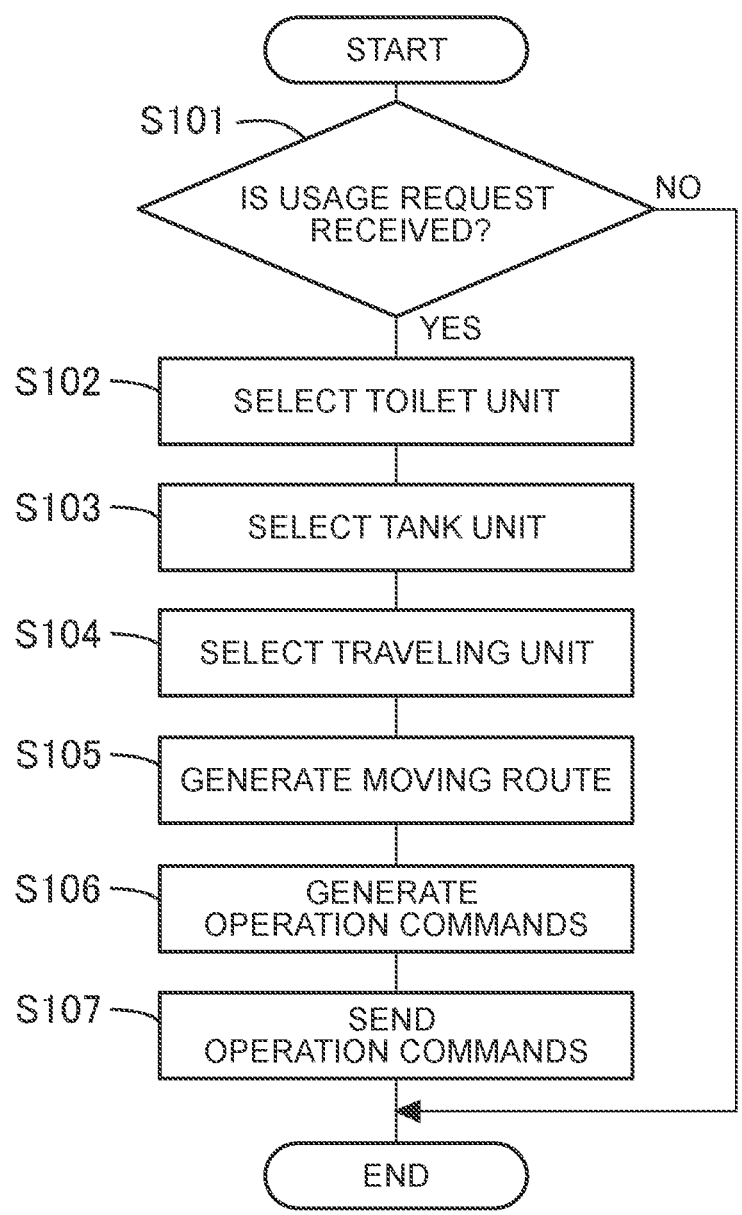
FIG. 11 shows an example of the flowchart of processing of the server when a temporary toilet is installed.

Next, the processing of the server 40 for installing a temporary toilet will be described below. FIG. 11 is an example of the flowchart of processing of the server 40 when a temporary toilet is installed. The processing shown in FIG. 11 is performed by the processor 41 of the server 40 at every predetermined time. In the description below, it is assumed that the server 40 has already received the information necessary to build the toilet unit information DB 411, the tank unit information DB 412, traveling unit information DB 413, and map information DB 414.

In step S101, the vehicle selection unit 402 determines whether a usage request is received from a user terminal. The usage request includes the information on the place where the toilet is to be installed. When the determination result of step S101 is Yes, the processing proceeds to step S102. When the determination result of step S101 is No, this routine is ended.

In step S102, the vehicle selection unit 402 selects the toilet unit 10 to be included in the temporary toilet. The vehicle selection unit 402 accesses the toilet unit information DB 411 and the map information DB 414 to select the toilet unit 10 nearest to the installation place of the temporary toilet.

In step S103, the vehicle selection unit 402 selects the tank unit 20 to be included in the temporary toilet. The vehicle selection unit 402 accesses the tank unit information DB 412 and the map information DB 414 to select the tank unit 20 nearest to the toilet unit 10 selected in step S102 or the tank unit 20 nearest to the installation place of the temporary toilet.

In step S104, the vehicle selection unit 402 selects the traveling unit 30. The vehicle selection unit 402 accesses the traveling unit information DB 413 and the map information DB 414 to select the traveling unit 30 nearest to the tank unit 20 selected in step S103. In place of the processing from step S102 to step S104, the vehicle selection unit 402 may select a combination of the toilet unit 10, the tank unit 20, and the traveling unit 30 that minimizes the moving distance of the traveling unit 30. After selecting the toilet unit 10, tank unit 20, and traveling unit 30, the vehicle selection unit 402 updates the toilet unit ID field and tank unit ID field of the traveling unit information DB 413.

Next, in step S105, the command generation unit 403 generates the moving route of the traveling unit 30 with the location of the tank unit 20 and the location of the toilet unit 10 as the waypoints. In this case, the starting location and the final destination of the traveling unit 30 may be, for example, a predetermined place (for example, the base of the vehicle). For example, the command generation unit 403 generates a moving route in such a way that the traveling unit 30 starts from the location of the traveling unit 30, then sequentially travels through the location of the tank unit 20, the location of the toilet unit 10, and the installation place of the temporary toilet, and then returns to the location where the traveling unit 30 started. The moving route is generated by referring to the map information DB 414. The moving route is a route generated according to the predetermined rule. After generating the moving route, the command generation unit 403 stores the generated moving route in the moving route field of the traveling unit information DB 413.

Then, in step S106, the command generation unit 403 generates operation commands including the moving route. The operation commands generated by the command generation unit 403 include the command that causes the traveling unit 30 to travel according to the moving route, the command that connects the tank unit 20 at the location of the tank unit 20, the command that connects the toilet unit 10 at the location of the toilet unit 10, and the command that disconnects the toilet unit 10 and the tank unit 20 at the installation place of the temporary toilet.

Then, in step S107, the command generation unit 403 sends the operation commands to the traveling unit 30.

Processing Flow When Installing Temporary Toilet: Traveling Unit

Figure 12:
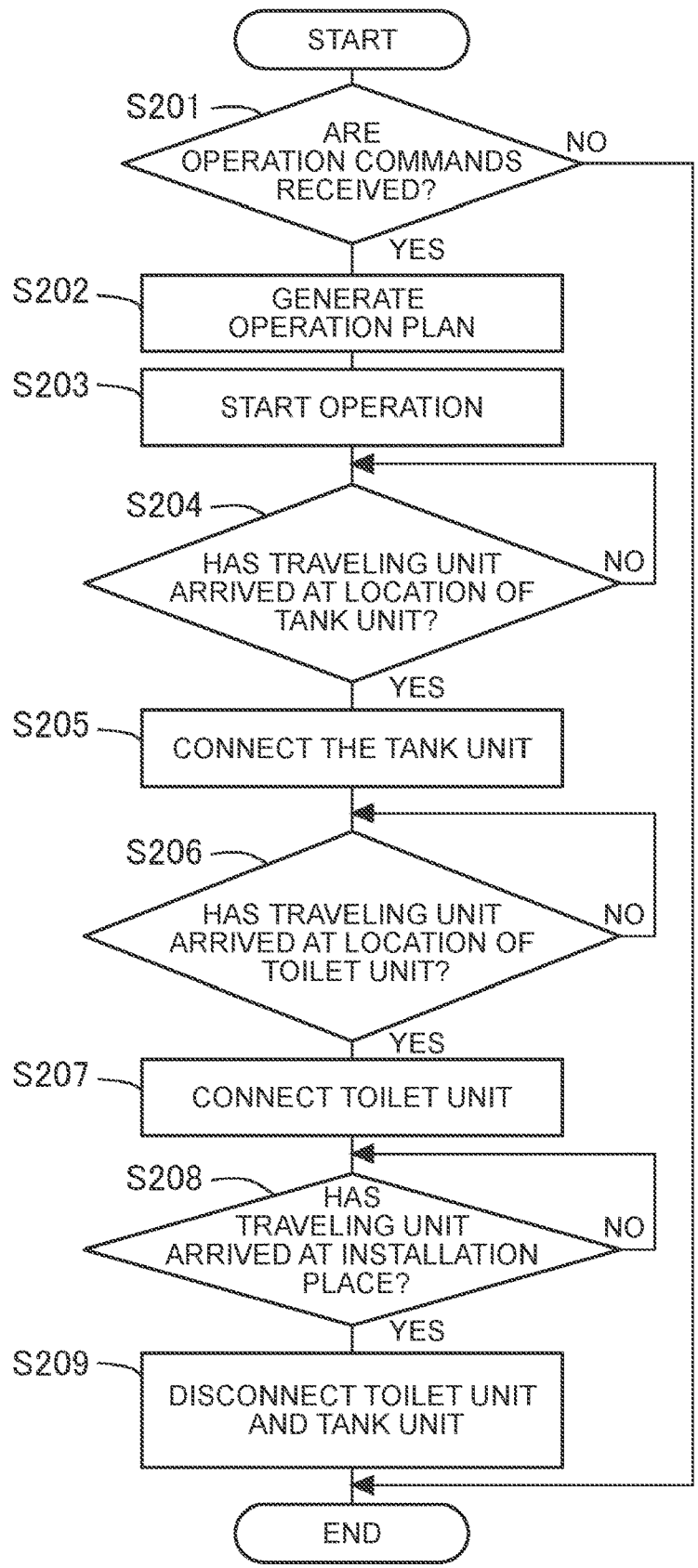
FIG. 12 shows an example of the flowchart of processing of the traveling unit according to the embodiment.

Next, the processing of the traveling unit 30 for installing a temporary toilet will be described. FIG. 12 shows an example of the flowchart of processing of the traveling unit 30 according to this embodiment. The processing shown in FIG. 12 is performed by the processor 31 of the traveling unit 30 at every predetermined time. The processing of this flowchart is performed when the traveling unit 30 is in the waiting state.

In step S201, the operation plan generation unit 301 determines whether operation commands are received from the server 40. When the determination result of step S201 is Yes, the processing proceeds to step S202. When the determination result of step S201 is No, this routine is ended. In step S202, the operation plan generation unit 301 generates an operation plan according to the operation commands. The operation plan includes a plan for traveling to the final destination via the waypoints.

After the generation of the operation plan is completed, the travel control unit 303 generates control commands in step S203. These control commands cause the drive unit 38 to start the operation of the traveling unit 30.

In step S204, the travel control unit 303 determines whether the traveling unit 30 has arrived at the location of the tank unit 20. For example, the traveling control unit 303 compares the position information, acquired by the position information sensor 36, with the information on the location of the tank unit 20, acquired from the server 40, to determine whether the traveling unit 30 has arrived at the location of the tank unit 20. When the determination result of step S204 is Yes, the processing proceeds to step S205. When the determination result of step S204 is No, the processing of step S204 is performed again.

In step S205, the connection management unit 305 issues the control command to the connection device 34 to connect the tank unit 20 and the traveling unit 30. For example, the operation command received from the server 40 includes a tank unit ID that allows the traveling unit 30 to determine the tank unit 20. For example, the traveling unit 30 may use the environment information sensor 37 to read the tank unit ID, indicated on the tank unit 20, for identifying the tank unit 20, or may communicate with the tank unit 20 for identifying the tank unit 20. The traveling unit 30 to which the tank unit 20 has been connected starts traveling toward the location of the toilet unit 10.

In step S206, the travel control unit 303 determines whether the traveling unit 30 has arrived at the location of the toilet unit 10. For example, the traveling control unit 303 compares the position information, acquired by the position information sensor 36, with the information on the location of the toilet unit 10, acquired from the server 40, to determine whether the traveling unit 30 has arrived at the location of the toilet unit 10. When the determination result of step S206 is Yes, the processing proceeds to step S207. When the determination result of step S206 is No, the processing of step S206 is performed again.

In step S207, the connection management unit 305 issues the control command to the connection device 34 to connect the toilet unit 10 and the traveling unit 30 with the tank unit 20 between them. For example, the operation command received from the server 40 includes a toilet unit ID that allows the traveling unit 30 to determine the tank unit 20. The traveling unit 30 may use the environment information sensor 37 to read the toilet unit ID, indicated on the toilet unit 10, for identifying the toilet unit 10. The traveling unit 30 to which the toilet unit 10 has been connected starts traveling toward the installation place of the temporary toilet.

In step S208, the travel control unit 303 determines whether the traveling unit 30 has arrived at the installation place of the temporary toilet. For example, the traveling control unit 303 compares the position information, acquired by the position information sensor 36, with the information on the installation place of the temporary toilet, acquired from the server 40, to determine whether the traveling unit 30 has arrived at the installation place of the temporary toilet. When the determination result of step S208 is Yes, the processing proceeds to step S209. When the determination result of step S208 is No, the processing of step S208 is performed again.

In step S209, the connection management unit 305 issues the control command to the connection device 34 to disconnect the toilet unit 10 and the tank unit 20 from the traveling unit 30. The traveling unit 30 from which the toilet unit 10 and the tank unit 20 have been disconnected starts traveling toward the base. In addition, the vehicle management unit 401 updates the traveling unit information DB 413 in such a way that the toilet unit ID field and the tank unit ID field corresponding to the traveling unit 30 are left blank.

Processing Flow When Replacing Tank Unit: Server

Figure 13:
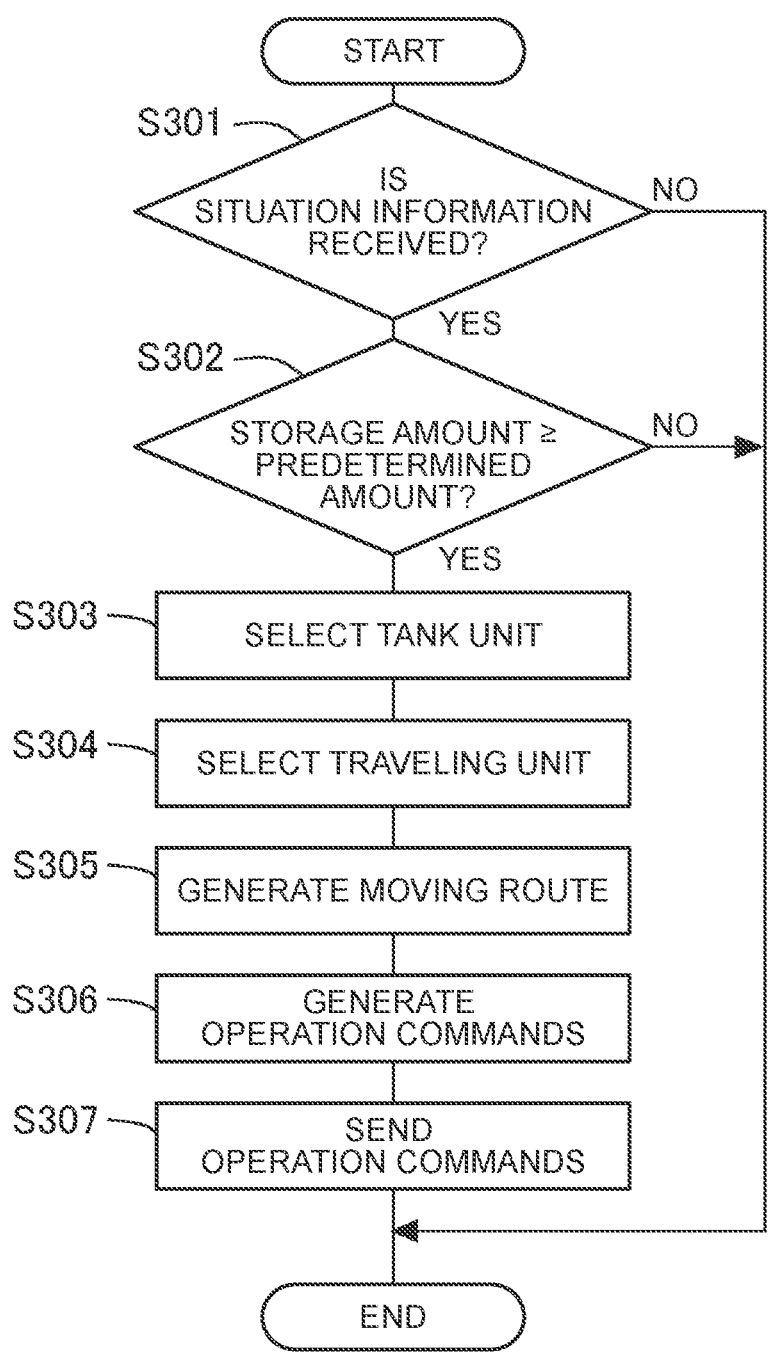
FIG. 13 shows an example of the flowchart of processing of the server when the tank unit is replaced.

Next, the processing of the server 40 for replacing the tank unit 20 will be described below. FIG. 13 shows an example of the flowchart of processing of the server 40 when the tank unit 20 is replaced. The processing shown in FIG. 13 is performed by the processor 41 of the server 40 at every predetermined time. In the description below, it is assumed that the server 40 has already received the information necessary to build the toilet unit information DB 411, the tank unit information DB 412, the traveling unit information DB 413, and the map information DB 414.

In step S301, the vehicle selection unit 402 determines whether the situation information is received from the tank unit 20. The situation information includes the detection value of the storage amount sensor 26 and the detection value of the odor sensor 11. When the determination result of step S301 is Yes, the processing proceeds to step S302. When the determination result of step 301 is No, this routine is ended.

In step S302, the vehicle selection unit 402 determines whether the storage amount of waste detected by the storage amount sensor 26 is equal to or larger than a predetermined amount. The predetermined amount is a threshold value for replacing the tank unit 20. Note that, in this step S302, the odor may be used instead of the storage amount. That is, the vehicle selection unit 402 may determine whether the degree of odor detected by the odor sensor 11 is equal to or larger than a predetermined value. The predetermined value is a threshold value for replacing the tank unit 20. In addition, the vehicle selection unit 402 may determine whether the storage amount of waste detected by the storage amount sensor 26 is equal to or larger than a predetermined amount or whether the degree of odor detected by the odor sensor 11 is equal to or larger than a predetermined value. The vehicle selection unit 402 may also determine whether the storage amount of waste detected by the storage amount sensor 26 is equal to or larger than a predetermined amount and whether the degree of odor detected by the odor sensor 11 is equal to or larger than a predetermined value. When the determination result of step S302 is Yes, the processing proceeds to step S303. When the determination result of step 302 is No, this routine is ended.

In step S303, the vehicle selection unit 402 selects the empty tank unit 20B. The vehicle selection unit 402 accesses the tank unit information DB 412 and the map information DB 414 to select, for example, the empty tank unit 20B nearest to the installation place of the toilet.

In step S304, the vehicle selection unit 402 selects the traveling unit 30. The vehicle selection unit 402 accesses the traveling unit information DB 413 and the map information DB 414 to select, for example, the traveling unit 30 nearest to the empty tank unit 20B selected in step S303. Instead of the processing of step S303 and step S304, the vehicle selection unit 402 may select a combination of the empty tank unit 20B and the traveling unit 30 in such a way that the moving distance of the traveling unit 30 is minimized. After selecting the empty tank unit 20B and the traveling unit 30, the vehicle selection unit 402 updates the tank unit ID field of the traveling unit information DB 413.

Next, in step S305, the command generation unit 403 generates a moving route of the traveling unit 30 with the location of the empty tank unit 20B as the waypoint. For example, the command generation unit 403 generates a moving route in such a way that the traveling unit 30 starts from the location of the traveling unit 30, then sequentially travels through the location of the empty tank unit 20B and the location of the tank unit to be replaced 20A, and then returns to the location where the traveling unit 30 started. The moving route is generated by referring to the map information DB 414. The generated moving route is a route generated according to the predetermined rule. After generating the moving route, the command generation unit 403 stores the generated moving route in the moving route field of the traveling unit information DB 413.

After that, in step S306, the command generation unit 403 generates operation commands including the generated moving route. The commands generated by the command generation unit 403 include the command that causes the traveling unit 30 to travel according to the moving route, the command that connects the empty tank unit 20B at the location of the empty tank unit 20B, and the command that replaces the tank unit to be replaced 20A with the empty tank unit 20B at the installation place of the temporary toilet.

After that, in step S307, the command generation unit 403 sends the operation commands to the traveling unit 30.

Processing Flow When Replacing Tank Unit: Traveling Unit

Figure 14:
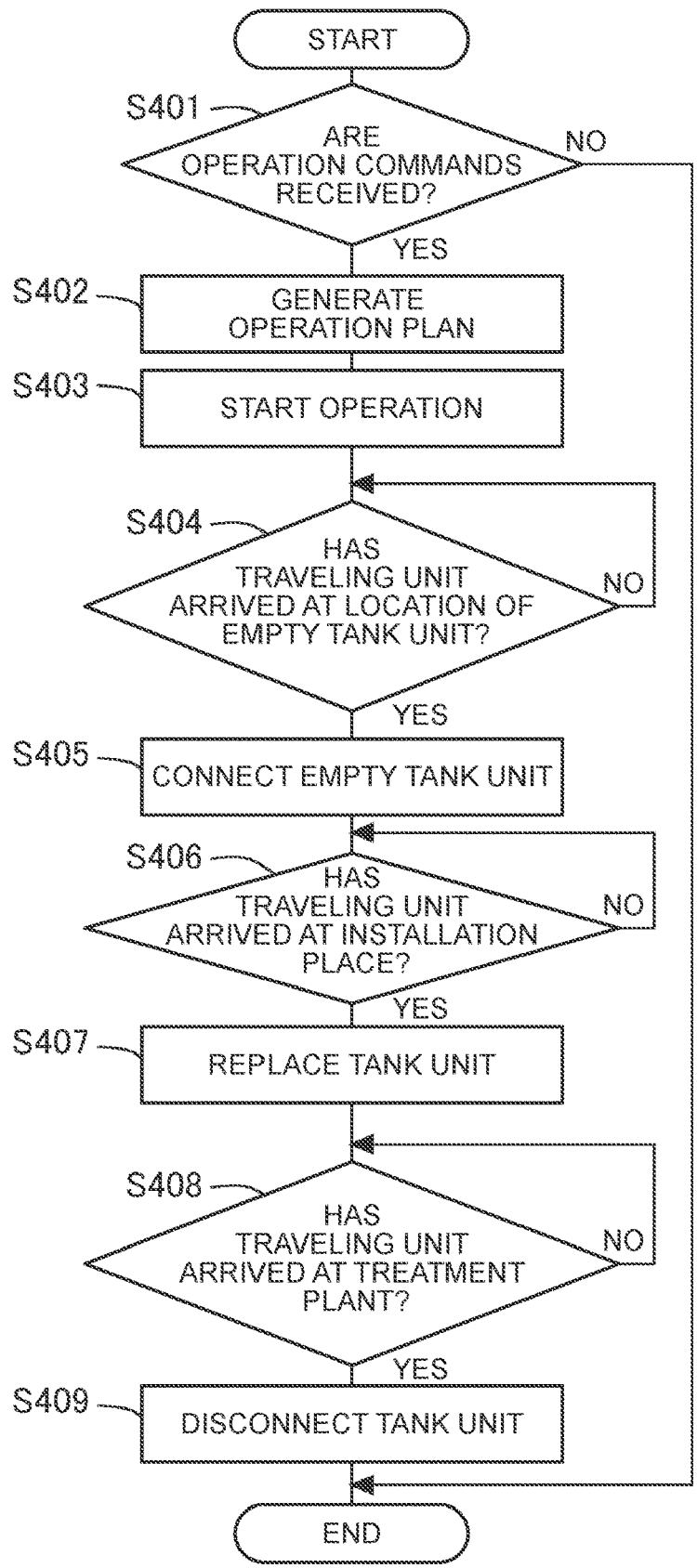
FIG. 14 shows an example of the flowchart of processing of the traveling unit according to the embodiment.

Next, the processing of the traveling unit 30 for replacing the tank unit 20 will be described below. FIG. 14 shows an example of the flowchart of processing of the traveling unit 30 in this embodiment. The processing shown in FIG. 14 is performed by the processor 31 of the traveling unit 30 at every predetermined time. The processing of this flowchart is performed when the traveling unit 30 is in the waiting state.

In step S401, the operation plan generation unit 301 determines whether the operation commands are received from the server 40. When the determination result of step S401 is Yes, the processing proceeds to step S402. When the determination result of step S401 is No, this routine is ended. In step S402, the operation plan generation unit 301 generates an operation plan according to the received operation commands. The operation plan includes a plan for traveling to the final destination via waypoints.

After the generation of the operation plan is completed, the travel control unit 303 generates control commands in step S403. These control commands cause the drive unit 38 to start the operation of the traveling unit 30.

In step S404, the travel control unit 303 determines whether the traveling unit 30 has arrived at the location of the empty tank unit 20B. For example, the traveling control unit 303 compares the position information, acquired by the position information sensor 36, with the information on the location of the empty tank unit 20B, acquired from the server 40, to determine whether the traveling unit 30 has arrived at the location of the empty tank unit 20B. When the determination result of step S404 is Yes, the processing proceeds to step S405. When the determination result of step S404 is No, the processing of step S404 is performed again.

In step S405, the connection management unit 305 issues the control command to the connection device 34 to connect the empty tank unit 20B and the traveling unit 30. The traveling unit 30 to which the empty tank unit 20B has been connected starts traveling toward the installation place of the temporary toilet.

In step S406, the travel control unit 303 determines whether the traveling unit 30 has arrived at the installation place of the temporary toilet. For example, the traveling control unit 303 compares the position information, acquired by the position information sensor 36, with the information on the installation place of the temporary toilet, acquired from the server 40, to determine whether the traveling unit 30 has arrived at the installation place of the temporary toilet. When the determination result of step S406 is Yes, the operation proceeds to step S407. When the determination result of step S406 is No, the processing of step S406 is performed again.

In step S407, the connection management unit 305 issues the control command to the connection device 34 to replace the tank unit to be replaced 20A with the empty tank unit 20B. The replacement method is not limited to a particular method but any replacement method may be used. The traveling unit 30, which has replaced the tank unit 20, starts traveling toward the treatment plant. The treatment plant is a place where the waste in the tank unit 20 is processed.

In step S408, the travel control unit 303 determines whether the traveling unit 30 has arrived at the treatment plant. For example, the travel control unit 303 compares the position information, acquired by the position information sensor 36, with the information on the treatment plant, acquired from the server 40, to determine whether the traveling unit 30 has arrived at the treatment plant. When the determination result of step S408 is Yes, the processing proceeds to step S409. When the determination result of step S408 is No, the processing of step S408 is performed again.

In step S409, the connection management unit 305 issues the control command to the connection device 34 to disconnect the tank unit 20. The traveling unit 30 from which the tank unit 20 has been disconnected starts traveling toward the base.

According to this embodiment, when the amount of waste stored in the tank unit 20 of a temporary toilet becomes equal to or larger than a predetermined amount, the traveling unit 30 replaces the tank unit 20 as described above, thus preventing the toilet unit 10 from being filled with odor. As a result, the temporary toilet can be used continuously. Replacing the tank unit 20 at an appropriate time in this way allows the temporary toilet to be used more favorably. In addition, the traveling unit 30 that has installed one temporary toilet can be used to carry another toilet unit 10 and another tank unit 20, meaning that a smaller number of traveling units 30 can operate more temporary toilets. In addition, this embodiment replaces the tank unit 20 according to the odor level of the toilet unit 10. This makes it possible to replace the tank unit 20 when the storage amount of waste is small but when the odor level is above a certain level, making the user feel more comfortable when using the toilet.

Other Embodiments

The above embodiment is merely an example, and the present disclosure may be modified as necessary for implementation without departing from the spirit of the present disclosure.

The processing and means described in the present disclosure can be freely combined for implementation as long as there is no technical contradiction.

Furthermore, the processing described as being performed by one device may be divided among two or more devices. Conversely, the processing described as being performed by different devices may be performed by one device. In a computer system, it is possible to flexibly change the hardware configuration (server configuration) to implement each function.

In the above embodiment, one traveling unit 30 is used to replace the tank unit 20. That is, one traveling unit 30 carries the empty tank unit 20B to the installation place of the temporary toilet and, then, carries the tank unit to be replaced 20A to the treatment plant. Instead of this, the tank unit to be replaced 20A and the empty tank unit 20B may be carried by different traveling units 30. In this case, the server 40 selects the traveling unit 30 that carries the tank unit to be replaced 20A and the traveling unit 30 that carries the empty tank unit 20B and, for each of them, generates operation commands.

The present disclosure can also be implemented by supplying a computer with a computer program that implements the functions described in the above embodiment and by causing one or more processors of the computer to read and execute the program. Such a computer program may be provided to the computer by a non-transitory computer-readable storage medium that can be connected to the system bus of the computer or may be provided to the computer via a network. The non-transitory computer-readable storage medium includes, for example, any type of disk, such as a magnetic disk (floppy (registered trademark) disk, hard disk drive (HDD), etc.) and an optical disc (CD-ROM, DVD disc, Blu-ray disc, etc.), and any type of medium suitable for storing electronic instructions such as a read only memory (ROM), a random access memory (RAM), an EPROM, an EEPROM, a magnetic card, a flash memory, and an optical card.

What is claimed is:

1. An information processing device for managing a vehicle including a toilet unit, a tank unit connected to the toilet unit for storing waste that flows from the toilet unit, and a traveling unit capable of moving the toilet unit and the tank unit, the information processing device being a device for performing control for disconnecting the traveling unit from the toilet unit and the tank unit when installing a toilet, the information processing device comprising a control unit configured to
acquire a storage amount of waste in the tank unit,
generate commands to the traveling unit to cause the traveling unit to replace the tank unit when the storage amount of waste becomes equal to or larger than a predetermined amount
acquire an odor of the toilet unit, and
generate commands to the traveling unit to cause the traveling unit to replace the tank unit when an odor equal to or larger than a predetermined value is detected regardless of the storage amount of waste.

2. The information processing device according to claim 1, wherein, when the toilet is installed, the control unit is configured to generate commands to the traveling unit to cause the traveling unit to sequentially travel through a location of the tank unit and a location of the toilet unit and then to travel toward an installation place of the toilet.

3. The information processing device according to claim 1, wherein, when the tank unit is replaced, the control unit is configured to generate commands to the traveling unit to cause the traveling unit to travel through a location of the tank unit and then to travel toward the installation place of the toilet.

4. The information processing device according to claim 3, wherein, when the tank unit is replaced, the control unit is configured to generate commands to the traveling unit to cause the traveling unit to connect to the tank unit that is empty at the location of the tank unit and then to travel toward the installation place of the toilet.

5. The information processing device according to claim 1, wherein, when the tank unit is replaced, the control unit is configured to generate commands to the traveling unit to cause the traveling unit to connect to a tank unit having a storage amount of waste equal to or larger than the predetermined amount at the installation place of the toilet and then to leave the installation place of the toilet.

6. The information processing device according to claim 1, wherein the control unit is configured to acquire the storage amount of waste of the tank unit from a sensor provided in the tank unit.

7. An information processing method for managing a vehicle including a toilet unit, a tank unit connected to the toilet unit for storing waste that flows from the toilet unit, and a traveling unit capable of moving the toilet unit and the tank unit, the information processing method being a method for performing control for disconnecting the traveling unit from the toilet unit and the tank unit when installing a toilet, the information processing method performed by a computer and comprising:
acquiring a storage amount of waste in the tank unit;
generating commands to the traveling unit to cause the traveling unit to replace the tank unit when the storage amount of waste becomes equal to or larger than a predetermined amount;
acquiring an odor of the toilet unit; and
generating commands to the traveling unit to cause the traveling unit to replace the tank unit when an odor equal to or larger than a predetermined value is detected regardless of the storage amount of waste.

8. The information processing method according to claim 7, wherein, when the toilet is installed, commands are generated to the traveling unit to cause the traveling unit to sequentially travel through a location of the tank unit and a location of the toilet unit and then to travel toward an installation place of the toilet.

9. The information processing method according to claim 7, wherein, when the tank unit is replaced, commands are generated to the traveling unit to cause the traveling unit to travel through a location of the tank unit and then to travel toward the installation place of the toilet.

10. The information processing method according to claim 9, wherein, when the tank unit is replaced, commands are generated to the traveling unit to cause the traveling unit to connect to the tank unit that is empty at the location of the tank unit and then to travel toward the installation place of the toilet.

11. The information processing method according to claim 7, wherein, when the tank unit is replaced, commands are generated to the traveling unit to cause the traveling unit to connect to a tank unit having a storage amount of waste equal to or larger than the predetermined amount at the installation place of the toilet and then to leave the installation place of the toilet.

12. The information processing method according to claim 7, wherein the storage amount of waste of the tank unit is acquired from a sensor provided in the tank unit.

13. A system comprising:
a vehicle including
a toilet unit,
a tank unit connected to the toilet unit for storing waste that flows from the toilet unit, and
a traveling unit capable of moving the toilet unit and the tank unit; and
a server including a control unit configured to perform control for disconnecting the traveling unit from the toilet unit and the tank unit when installing a toilet, wherein the control unit is configured to
acquire a storage amount of waste in the tank unit,
generate commands to the traveling unit to cause the traveling unit to replace the tank unit when the storage amount of waste becomes equal to or larger than a predetermined amount
acquire an odor of the toilet unit, and
generate commands to the traveling unit to cause the traveling unit to replace the tank unit when an odor equal to or larger than a predetermined value is detected regardless of the storage amount of waste.

14. The system according to claim 13, wherein, when the toilet is installed, the control unit is configured to generate commands to the traveling unit to cause the traveling unit to sequentially travel through a location of the tank unit and a location of the toilet unit and then to travel toward an installation place of the toilet.

15. The system according to claim 13, wherein, when the tank unit is replaced, the control unit is configured to generate commands to the traveling unit to cause the traveling unit to travel through a location of the tank unit and then to travel toward the installation place of the toilet.

16. The system according to claim 15, wherein, when the tank unit is replaced, the control unit is configured to generate commands to the traveling unit to cause the traveling unit to connect to the tank unit that is empty at the location of the tank unit and then to travel toward the installation place of the toilet.

17. The system according to claim 13, wherein, when the tank unit is replaced, the control unit is configured to generate commands to the traveling unit to cause the traveling unit to connect to a tank unit having a storage amount of waste equal to or larger than the predetermined amount at the installation place of the toilet and then to leave the installation place of the toilet.

18. The system according to claim 13, wherein the control unit is configured to acquire the storage amount of waste of the tank unit from a sensor provided in the tank unit.

* * * * *